US012114968B2

(12) United States Patent
Kaditz et al.

(10) Patent No.: US 12,114,968 B2
(45) Date of Patent: Oct. 15, 2024

(54) SYSTEM AND METHOD FOR MAGNETIC RESONANCE ELASTOGRAPHY

(71) Applicant: Q Bio, Inc., San Carlos, CA (US)

(72) Inventors: Jeffrey H. Kaditz, Wilson, WY (US); Andrew G. Stevens, Palo Alto, CA (US)

(73) Assignee: Q Bio, Inc., San Carlos, CA (US)

( * ) Notice: Subject to any disclaimer, the term of this patent is extended or adjusted under 35 U.S.C. 154(b) by 0 days.

(21) Appl. No.: 18/526,806

(22) Filed: Dec. 1, 2023

(65) Prior Publication Data
US 2024/0099603 A1 Mar. 28, 2024

Related U.S. Application Data

(63) Continuation of application No. 16/085,877, filed as application No. PCT/US2017/022911 on Mar. 17, 2017, now Pat. No. 11,872,025.
(Continued)

(51) Int. Cl.
*A61B 5/055* (2006.01)
*G01R 33/341* (2006.01)
(Continued)

(52) U.S. Cl.
CPC .......... *A61B 5/055* (2013.01); *G01R 33/341* (2013.01); *G01R 33/56358* (2013.01); *G06T 7/0012* (2013.01)

(58) Field of Classification Search
None
See application file for complete search history.

(56) References Cited

U.S. PATENT DOCUMENTS

| 4,729,892 A | 3/1988 | Beall |
| 5,865,177 A * | 2/1999 | Segawa .................. A61B 5/055 324/318 |

(Continued)

FOREIGN PATENT DOCUMENTS

EP    3093677    11/2016

OTHER PUBLICATIONS

Klucinec, B. The effectiveness of the aquaflex gel pad in the transmission of acoustic energy. Journal of athletic training, (1996). 31(4), 313. (Year: 1996).*
(Continued)

*Primary Examiner* — Christopher Koharski
*Assistant Examiner* — Renee C Langhals
(74) *Attorney, Agent, or Firm* — Aurora Consulting LLC; Steven E. Stupp; Ashley Sloat

(57) ABSTRACT

A system for MR Elastography of a sample, including ultrasound gel to sheath the sample, a vessel to accept the flow of the sample sheathed in ultrasound gel, a sensor array adapted to capture an ultrasound measurement and an MR measurement, wherein the sensor array including an ultrasound transmitter and an ultrasound receiver, and the sensor array is coupled to the vessel, and the vessel is capable of mechanical conductance between the ultrasound transducers, and the ultrasound gel, and a pump to create a pressure based flow of ultrasound fluid through the vessel and move the sample in proximity to the sensor array for capture of MR and ultrasound measurements of the sample as the sheathed sample passes by the sensor array.

20 Claims, 7 Drawing Sheets

Related U.S. Application Data

(60) Provisional application No. 62/310,667, filed on Mar. 18, 2016.

(51) Int. Cl.
  *G01R 33/563* (2006.01)
  *G06T 7/00* (2017.01)

(56) References Cited

U.S. PATENT DOCUMENTS

| | | | |
|---|---|---|---|
| 2011/0166484 A1 | 7/2011 | Virta | |
| 2015/0309140 A1 | 10/2015 | Trzasko et al. | |
| 2016/0007968 A1* | 1/2016 | Sinkus | G01R 33/56358 600/407 |
| 2016/0030009 A1* | 2/2016 | Hoelscher | A61B 8/4477 600/458 |
| 2017/0246482 A1 | 8/2017 | Hananel et al. | |

OTHER PUBLICATIONS

"Gualda et al. SPIM-fluid: open source light-sheet based platform for high-throughput imaging. Biomed Opt Express (Nov. 1, 2015} vol. 6, No. 11, pp. 4447-4456, p. 4448 para 2-3, p. 4450, para 2".

"Hornak, J. article entitled "The Basics of MRI," http://www.cis.rit.edu/htbooks/mri/inside.htm".

"International Application Serial No. PCT/US2017/022911, International Search Report mailed Jul. 19, 2017", 4 pgs.

"International Application Serial No. PCT/US2017/022911, Written Opinion mailed Jul. 19, 2017", 10 pgs.

"Klucinec, B., "The Effectiveness of the Aquaflex Gel Pad in the Transmission of Acoustic Energy," Journal of Athletic Training, 1996:31(4):313-317".

"Siemens. Magnetic Resonance Imaging. (Dec. 2012) [retrieved on Jun. 27, 2017, https://w5.siemens.com/web/ua/ru/medecine/detection_diagnosis/magnetic_resonans/035-15-MRI-scaners/Documents/mri-magnetom-family_brochure-00289718.pdf] p. 6-8, 13, 15-16".

Hattori, K., Ikemoto, Y., Takao, W., Ohno, S., Harimoto, T., Kanazawa, S., . . . & Kato, H. (2013). Development of MRI phantom equivalent to human tissues for 3.0-T Mri. Medical physics, 40(3), 032303 (Year: 2013).

* cited by examiner

SYSTEM AND METHOD FOR MAGNETIC RESONANCE ELASTOGRAPHY

CROSS REFERENCE TO RELATED APPLICATIONS

This application is a Continuation of U.S. Non-Provisional Application Ser. No. 16/085,877, entitled "System and Method for Magnetic Resonance Elastography," filed Sep. 17, 2018, which claims priority under 35 U.S.C. § 119 (e) to U.S. Provisional Application Ser. No. 62/310,667, entitled "System and Method for MR Elastography," filed Mar. 18, 2016, the contents of both of which is are herein incorporated by reference in their entirety.

FIELD

The described embodiments relate generally to medical imaging, more specifically to Magnetic Resonance imaging (MRI), ultrasonic imaging (e.g. ultrasound), and Magnetic Resonance Spectral Imaging (MRSI) when discussing spectrums beyond just the Hydrogen ($^1H$) spectrum, and more specifically to techniques for scanning, capturing, searching, aggregating and processing MRI data, and providing medical information services and medical services based on the captured and aggregated MR data.

RELATED ART

Generally, most tissue samples in hospitals are evaluated by a medical specialist and then destroyed, with a few symptomatic samples being preserved for medical research purposes. Presently, there are no large standardized datasets that contain routinely symptomatic and asymptomatic tissue samples for comparison and improvement of medical diagnoses.

SUMMARY

Trends in connectivity and in medical imaging technology are resulting in dramatic changes in people's lives. For example, the Internet now allows doctors, researchers, and data scientists to access vast amounts of anonymized information, as well as the ability to interact with individual patients and provide diagnoses around the world. This remote electronic capability has improved the quality of healthcare and reduced costs. Similarly, the increasingly powerful computing and communication capabilities of cloud computing and infrastructure as a service (IAAS) product offerings from companies such as Amazon Web Services and Cloudera combined with portable electronic devices (such as smartphones and tablets), as well as a large and growing set of applications, are accelerating these improvements, and the ability to leverage medical information to perform a wide variety of diagnoses.

As imaging technology improves both higher resolution information as well as new types of information can be measured, which drives an ever-increasing trend of specialization in radiology. The invention described herein includes a system and methods for magnetic resonance Elastography of biological life forms and of biological samples (including fresh "wet" tissue samples, frozen samples, formalin fixed—paraffin embedded (FFPE) samples) to create a large database of symptomatic and asymptomatic Magnetic Resonance signature data for use in automatically detecting anomalies and healthy tissue, performing more detailed scans of detected anomalies, and either automatically classifying between anomalies and healthy tissue using a software algorithm and/or providing the images to radiologists who specialize in the type of tissue or anomaly detected for verification and/or identification. The tissue sample signatures can be applied to better detect anomalies on an individual basis; what is normal in one body might be slightly different than what is normal in another body, and clusters of tissue samples reflecting various shades of normal can help classify tissue. Finally, the amount of data that can be captured about each sample is much larger than the amount of data that can be processed by a single pathologist or radiologist or even a team of radiologists and pathologists. One goal of the invention is to be able to provide hospitals and research institutions with this device in order for the institutions to catalogue and index all of their tissue samples, and contribute to building a large database of signatures of indexed tissues covering both symptomatic and asymptomatic tissue samples.

For a few decades MRI technology has been the imaging modality of choice for soft tissue and morphological studies. As field strengths have continued to rise, the technical feasibility of MR Spectroscopy has been demonstrated, opening the possibility for MRSI to do both morphological and functional imaging in parallel. The technology facilitates high spatial and spectral resolution sample indexing and can also incorporate capturing signatures of Magnetic Resonance which can measure quantitative profiles of specific tissues of both symptomatic and asymptomatic tissue, such as tissue samples from biopsies, whether benign or non-benign, and can detect known healthy (i.e., whitelisted tissue) and known anomalous tissue (i.e., blacklisted tissue) and classify unknown tissue in a grey zone (i.e., greylisted tissue), which can be marked for inspection by other MR spectra, additional related biopsies, inspection by a radiologist, pathologist or other analysis as may be determined to be necessary.

In some embodiments scans can also include MR Elastography, which measures the stiffness of tissue by sending mechanical waves through the tissue with an MRI technique including sending shear waves in the tissue, acquiring images of the propagation of the shear waves, and processing the images of the shear waves to produce a quantitative mapping of the tissue stiffness, which are known in the literature as elastograms.

This document outlines a system to perform MR Elastography (using an ultrasonic wave generator) on both biological life forms and tissue samples. Another unique aspect of this system is that it is optimized to screen both symptomatic and asymptomatic tissue samples, as it is just as important to recognize healthy tissue, as it is to recognize pathology.

In this model, each voxel in the sample in the MR scan has multi-dimensional data on the volumetric density of certain chemical signatures and atomic nuclei. This system can be aware of the region of the body, or the source of the sample in which a sample originated, and can use that knowledge to further optimize the configuration to best collect information about the sample. Additionally, the system can be used to scan multiple samples, from the same subject or different subjects can be scanned simultaneously, if increased throughput is needed.

In a first embodiment, a platform for use in an MR system for capturing an MR Elastography measurement of a biological life form can include a sensor array, wherein the sensor array comprises at least one ultrasound transducer; at least one RF transmitter; a receiver coil for an MR system; and a gel pad on the platform, wherein the sensor array is embedded within the gel pad, and the gel pad provides a mechanical impedance matching between the ultrasound transducers of the sensor array and the biological life form.

In a second embodiment, a system for MR Elastography of a sample includes an ultrasound gel, adapted to sheath the sample; a vessel, adapted to accept the flow of the sample sheathed in ultrasound gel; a sensor array adapted to capture at least one ultrasound measurement and at least one MR measurement, wherein the sensor array comprises at least one ultrasound transmitter and at least one ultrasound receiver, wherein the sensor array is coupled to the vessel, and wherein the vessel is capable of mechanical impedance matching between the ultrasound transducers, and the ultrasound gel; and at least one pump to create a pressure based flow of ultrasound fluid through the vessel and move the sample in proximity to the sensor array for capture of MR and ultrasound measurements of the sample as the sheathed sample passes by the sensor array.

In a third embodiment, a method of capturing an MR Elastography measurement of a sample includes sheathing the sample in an ultrasound fluid; feeding the sample sheathed in ultrasound fluid through a vessel; controlling the flow of the ultrasound fluid in the vessel such that the sample is moved in proximity to a sensor array, wherein the sensor array comprises at least one ultrasound transmitter and receiver, and at least one MR sensor system; capturing both MR measurements and ultrasound measurements from the sensor array; and generating an MR Elastogram from the resulting measurements.

Some embodiments may include an ultrasonic wave generator, and the program module may include instructions for performing MR Elastography on the sample. In some embodiments, the MR scanner is a bore scanner, and the ultrasonic wave generator generates waves at the ends of the bore of the MR scanner.

The preceding summary is provided as an overview of some exemplary embodiments and to provide a basic understanding of aspects of the subject matter described herein. Accordingly, the above-described features are merely examples and should not be construed as narrowing the scope or spirit of the subject matter described herein in any way. Other features, aspects, and advantages of the subject matter described herein will become apparent from the following Detailed Description, Figures, and Claims.

DETAILED DESCRIPTION

Figure 1:
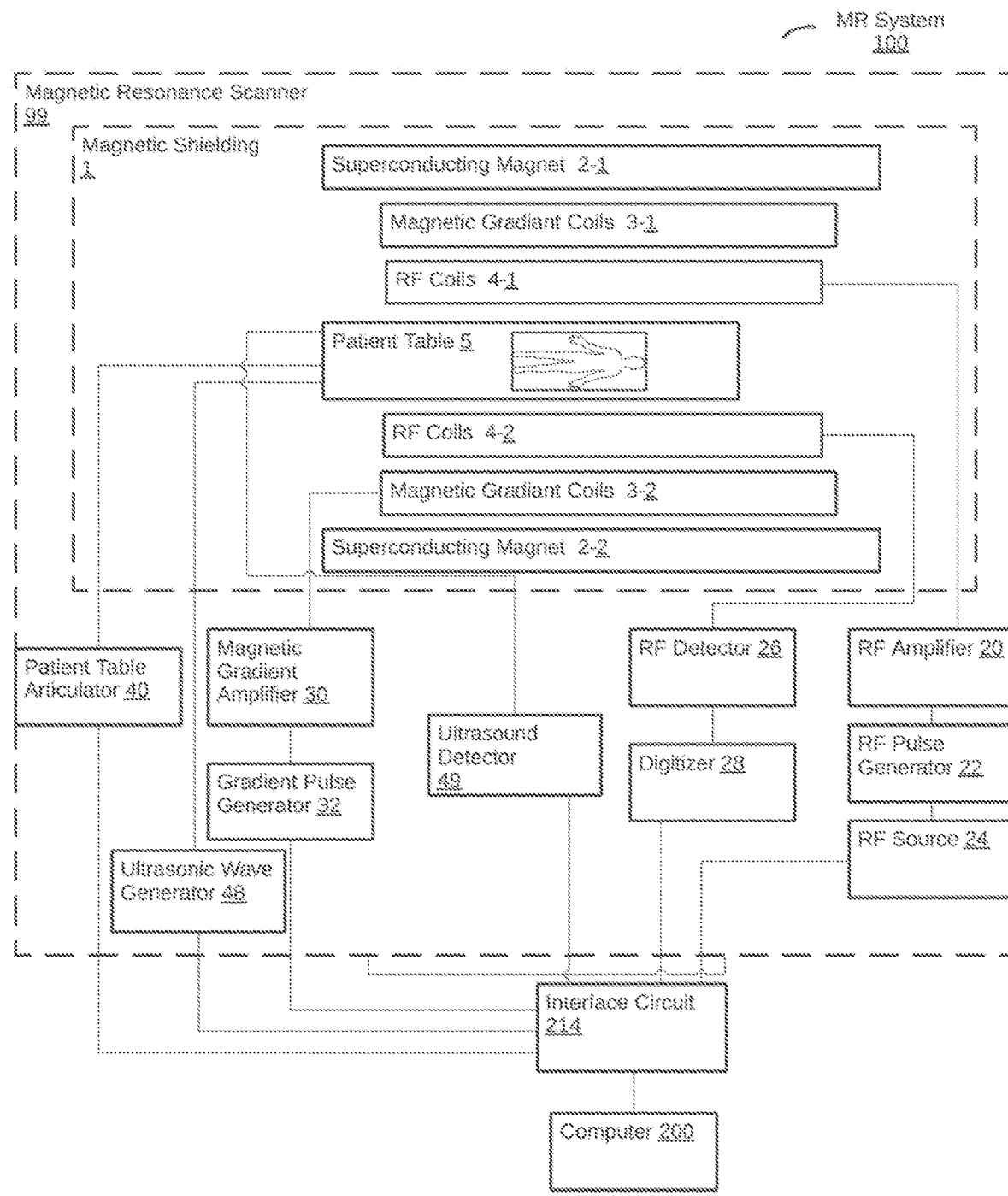
FIG. 1 is a block diagram illustrating a magnetic resonance scanner equipped with an ultrasonic wave generator adapted for humans or animals.

The invention described herein includes a system and methods for magnetic resonance Elastography of biological life forms and of biological samples (including fresh "wet" tissue samples, frozen samples, formalin fixed—paraffin embedded (FFPE) samples) to create a large database of symptomatic and asymptomatic Magnetic Resonance Field Invariant Signature data for use in automatically detecting anomalies and healthy tissue, performing more detailed scans of detected anomalies, and either automatically classifying between anomalies and healthy tissue using a software algorithm and/or provide the images to radiologists who specialize in the type of tissue or anomaly detected for verification and/or identification, and especially relating to MR Elastography.

A scan can also include MR Elastography, which measures the stiffness of tissue by sending mechanical waves through the tissue with an MRI technique including sending shear waves in the tissue, acquiring images of the propagation of the shear waves, and processing the images of the shear waves to produce quantitative mapping of the tissue stiffness, which are called elastograms.

As medical imaging and other medical diagnostic technology improves, both higher resolution information as well as new types of information can be measured quantitatively which drives an ever-increasing trend of specialization in radiology and other medical diagnostic techniques. The invention described herein includes a system and methods for using a combination of magnetic resonance techniques including but not limited to MR signature capture, Morphology scanning, Elastography, Spectroscopy, Thermometry, and Diffusion Tensor mapping. This capability can help diagnostics determine which parts of tissue in vivo may require more detailed scans of detected anomalies by either algorithmically classifying anomalies as healthy/unhealthy tissue and/or providing the images to radiologists who specialize in the type of tissue or anomaly detected for verification and/or identification. Finally, the amount of data that can be captured about each sample is much larger than the amount of data that can be processed by a single pathologist or radiologist or even a team of radiologists and pathologists.

Scanning of tissue samples can be performed by many types of MR scanners (including cryo and non-cryo MRI systems, low field imaging systems that use lower field strength magnets), as well as other types of medical imaging devices, including ultrasounds and CT tomography. Images can be individual 2-dimensional images, such as MRI scans, or X-rays or CT scans, or can include 3-D models determined from voxels in MRI scans and/or other image processing techniques, and can include animations of a body or a portion of a body over time (e.g. over weeks, months or years, or during a surgery). Additionally, MR Signature detection can be used to scan tissue samples. Tissue sample scans can be tied to optical, thermal sensors, and scans can also include one or more spectra, one or more voxel sizes, one or more MR modalities, one or more $B_0$ or $B_1$ field strengths, or one or more ultrasound techniques. Any pulse sequence can be used, and while certain pulse sequences can have effects, the techniques described in this disclosure are not dependent on the use of any particular pulse sequence.

Figure 2:
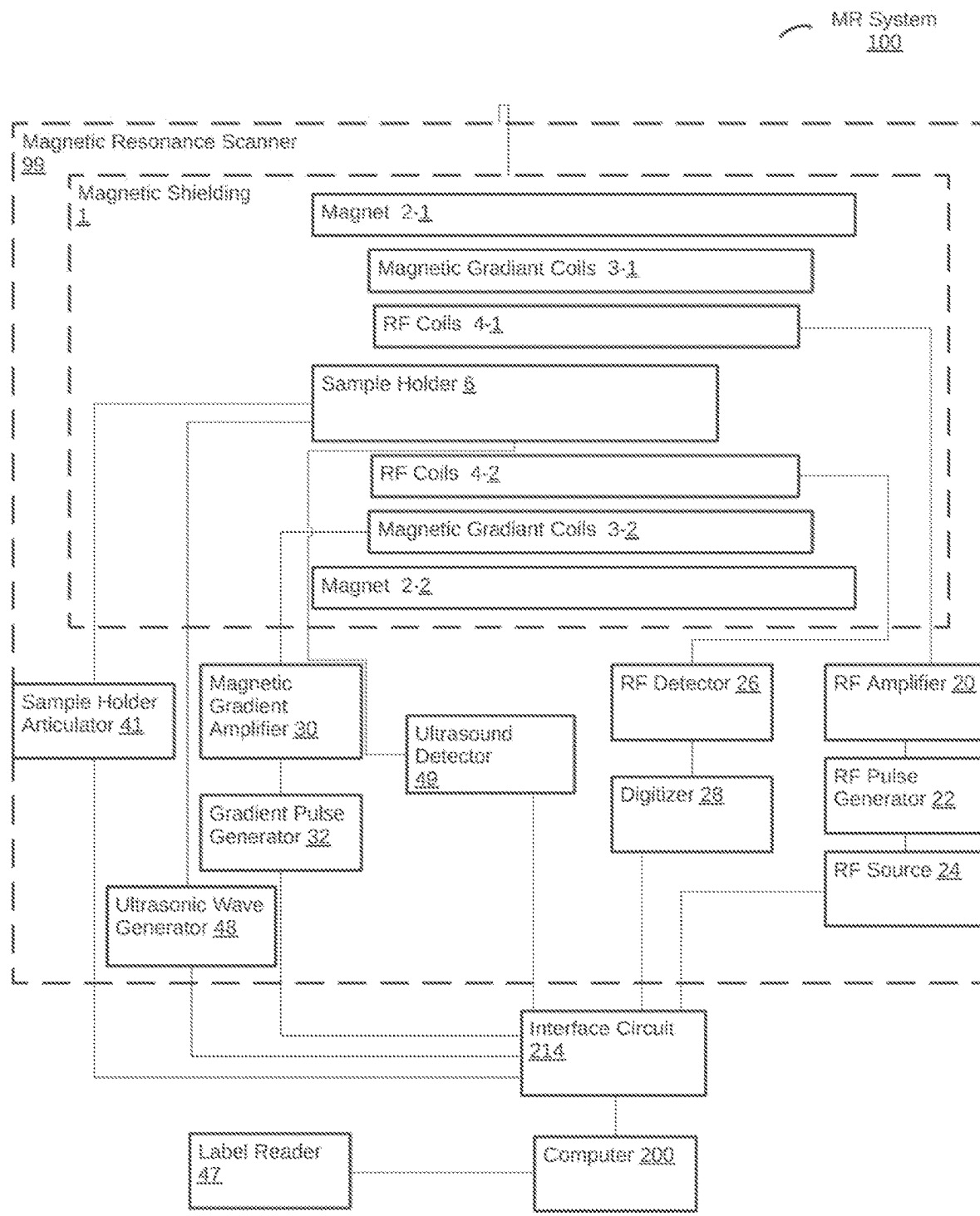
FIG. 2 is a block diagram illustrating a magnetic resonance scanner equipped with an ultrasonic wave generator adapted for biological samples.

By way of introduction and definition, we now describe the basic functionality for a standard MR system 100. In a first group of embodiments, as shown in FIGS. 1-2, an MR system 100 includes a Magnetic Resonance (MR) Scanner 99, which includes magnetic shielding 1, a magnet 2, magnetic gradient coils 3, RF coils 4, a patient table 5 (or a sample holder 6) an RF amplifier 20, an RF pulse generator 22, an RF source 24, an RF detector 26, a digitizer 28, a magnetic gradient amplifier 30, a gradient pulse generator 32, a patient table articulator 40 (or a sample holder articulator 41), an ultrasonic wave generator 48, and an ultrasound detector 49, all connected through an interface circuit 214 to a computer 200, which can control the components of the MR scanner via control mechanisms, program modules, processor implemented methods, and the like. These components of the MR scanner 99 are described briefly below, but more detail is available in Chapter 9 of "The Basics of MM" by Dr. Joseph P. Hornak, and is currently available online at http://www.cis.rit.edu/htbooks/mri/inside.htm, and incorporated herein by reference.

The MR system 99 as shown in FIG. 1 can be a closed bore or an open bore system. The magnet 2 (shown as a cutaway in 2 portions 2-2, and 2-1) can be either closed bore or open bore. An open bore system can utilize a magnetic field between two plates, and can be low field (e.g. less than 0.1 Tesla) strong ferromagnetic magnets (approximately 0.5 T) or high field (over 1 Tesla) depending on the imaging technology to be used for diagnosis. A closed bore system can include a toroid shaped (or in layman's terms a donut shaped) magnet and the patient or sample can be moved through the hole in the center of the toroid (thus exposing the patient or the sample to the strong magnetic field), and systems are generally horizontal (known as horizontal bore) moving the sample horizontally through the field, but can also be vertically oriented. An open bore system is a gap between two plates, and the patient can be moved between the plates, and exposed to a strong magnetic field between the plates. The MR system 99 can be applied to MR scanners that scan patients and/or samples in various positions, including multiple angles, orientations and perspectives.

The magnet 2 can be a superconducting magnet and superconducting magnets are the most common types of magnets used. However, any suitably strong magnet may be used, and configurations of magnets 2 that can work at room temperatures are known in the art. Magnets down to 0.001 T can be used at room temperature in open bore configurations, and can have the added effect of imaging metallic objects due to their low field. The magnet 2 is most commonly closed bore, and made from a coil of Niobium Titanium (NbTi) wire or Niobium Tin ($Nb_3Sn$) wire, both Type II semiconductors, and the amount of wire used can typically be several miles. The wire coil is kept at a superconducting temperature of 4.2 Kelvin by insulating it in liquid Helium (He). In some systems, the liquid helium is insulated and thermally buffered by liquid nitrogen (N) to prevent boiling off of the He, and in some systems a refrigerated or otherwise cooled dewar is used, to contain the liquid He for periods of up to 3-4 years. There are currently efforts researching using liquid hydrogen since there is finite supply of helium on earth, different coolants may be used to cool the coils and rooms. The purpose of the superconducting magnet 2 in the MR system is to create a very strong magnetic field, referred to hereafter as $B_0$(B-nought) and align the spins of nuclei when they are exposed to the strong magnetic field. The magnet 2 can be a smaller bore magnet from 1 cm to 10 cm or 5 cm to 30 cm, but can also be any suitable size. In some embodiments, smaller magnets may be used for processing medical samples and biopsies. For example, with a smaller magnet 2, it becomes possible that the entire MR scanner 99 including the computer 200, can fit on a wheeled cart and can be wheeled between rooms or departments in a medical facility such as a clinic, hospital or research institution.

The magnetic shielding 1 can be composed of steel plates, or it can be composed of silicon steel in the form of metal sheets, with the latter being easier to work with. The shielding 1 can be placed all around a room, fully covering walls, floors and ceilings, with the main purpose being to attenuate the field strength to below 5-gauss as per the FDA recommended guidelines. Special doors and doorframe seals can be used to further reduce the field that can leak out of the room. Alternatively, some magnets include shielding on the magnet to reduce the fringe field, with known examples in operation in the field dropping to 0.5 mT at a range of 4 meters from the magnet. This reduces the need for magnetic shielding, and depending on the site, may eliminate the need for magnetic shielding entirely. The shielding on the magnet is achieved by including a second set of windings (also superconducting) operating with opposite current flow outside the main superconducting windings to reduce the fringe field by canceling out the magnetic field.

The magnetic shielding 1 can also function as a chamber and can be a sealed chamber, such that an Ultrasound receiver 49, as shown in FIGS. 1-2, can be coupled to a vacuum pump and used to remove air from the chamber, (e.g. create a vacuum chamber), or alternatively the Ultrasound receiver 49 can be coupled to a gas tank and the chamber can be flooded with an inert gas, such as Xenon to improve MR imaging quality, and the inert gas can be polarized.

The magnetic gradient coils 3 typically operate at room temperature and function to produce gradients in $B_0$. Typically, in horizontal bore systems, using standard magnetic resonance coordinates, a gradient in $B_0$ in the Z direction is achieved with an anti-Helmholtz coil, with current in each coil adding or subtracting to $B_0$ to achieve a gradient. The X and Y gradients can be created by a pair of FIG. 8 coils, creating gradients along their respective axes. Gradient coil strengths are typically 100 mT/m and have fast switching times, also known as slew rates of 150 mT/m/ms, enabling 0.7 mm slice thickness and 0.1 mm voxel resolution in 3D imaging. In the U.S., slew rate limits are currently set at 200 T/m/s, with higher slew rates causing nerve stimulation. However, recent research has shown that, at frequencies above approximately 100 kHz (corresponding to a rise-time below 10 microseconds, and corresponding to a slew rate of 160,000 T/m/s), no nerve stimulation occurred, even with varying pulse shapes. Stronger magnets (7 Tesla for example) provide improved 3-dimensional imaging measurements down to 60 micrometers in isometric voxel sizes.

The magnetic gradient amplifier 30 functions to increate the power of the gradient pulses to a level suitable for driving the gradient coils. The magnetic gradient pulse generator 32 functions to produce the shape and amplitude of the gradient field in each of the 3 gradient fields (X, Y, and Z in standard MRI coordinates). The magnetic gradient amplifier 30 and the magnetic gradient pulse generator 32 are both controlled by the computer 200 via an interface circuit 214.

The RF coils 4 create a $B_1$ field that rotates the net magnetization in a pulse sequence. They also detect transverse magnetization as it processes in the XY plane. RF coils 4 can transmit only, receive only or can function as both transmitter and receiver. The RF coils 4 need to be oriented such that the $B_1$ field is perpendicular to the $B_0$ field. The RF coils 4 can be tuned to the Larmor frequency (e.g. resonant frequency of a nuclei being imaged at $B_0$) by adjusting the capacitor or inductor, but generally varying capacity capacitors and inductors are used (matching and tuning capacitors). Any number or type of RF coils can be used including an Alderman-Grant Coil, Bird Cage, Butterfly Coil, Dome Resonator, Gradiometer, Implantable Coil, Inside Out/ Schlumberger Coil, Intravascular Coil, Ladder Coil, Litz Coil, Loop-Gap Resonator Coil, Loop-Stick-Coil, Meanderline Coil, Mouse Coil, Multi-Turn Solenoid Coil, Phased Array Coil, Phased Array Volume Coil, Ribbonator Coil, Saddle Coil, Scroll Coil, Single Turn Solenoid Coil, Spiral Coil, Superconducting Coil, Transmission line coil, Truncated Spiral Coil, and 3-Axis coil. Birdcage coils are typically used for volume, single turn solenoid coils are typically used for extremities, and surface coils (receive only) are commonly used for body imaging because they give a good Signal to Noise Ratio (SNR) of tissues and samples adjacent to the coil. Additionally, wide-band RF coil transmitters can be used to excite multiple spectra simultaneously, and can be used with wideband RF receiving coils.

The coils can include thermal imaging sensors, which can include a forward-looking infrared (FLIR) sensor. The additional sensors can be attached modularly (either snapped together in concentric shells, or snapped on additions, assembled with interlocking interfaces, and can communicate with each other via wireless or wired connections. As one or more sensors pass regulatory approval, they can graduate from research to commercial use and be added onto a coil for commercial applications.

Additionally, in one variation, surface coils that can be controlled by software executing the scan plan such that certain modalities can be turned off and on in real-time as determined by analysis of the sample, e.g. to take an MR Elastography measurement of the anomaly, a thermal image of the sample, or the surrounding region. In this example, the coils can be constructed to include multiple sensors and data collection equipment to be used for specialized anomaly detection. For example, the MR RF coils can be optimized for parallel collection of data by MR Thermometry, MR Field Invariant Signature Detection MR Spectroscopy, MR Elastography, Multi-nuclear imaging of two or more nuclei ($^1$H, $^{23}$Na, $^{31}$P, $^{13}$C, $^{19}$F, $^{39}$K, $^{43}$Ca) Diffusion Tensor Imaging, or N-channel scanning.

In one embodiment, the readings from coils can be digitized within or just outside of the coil assembly and transmitted wirelessly to a computer 200 to avoid messy cable tangling, and without creating significant RF noise in the frequencies of interest, which can include transmitting data to the computer 200 at lower or higher frequencies than the $\gamma B_0$ frequencies of the targeted nuclei in the MR field invariant signature detection, outside of the frequencies measured, and filtering inputs and outputs and noise artifacts.

The RF amplifier 20 increases the power of the RF pulses to be strong enough to drive the RF coils, typically increasing the power from mW to kW. The RF amplifier 20 receives signals from the RF pulse generator 22 and/or the RF source 24. The RF source 24 produces sinewaves of the desired frequencies (e.g. tuned for desired nuclei and $B_0$ field strength). The RF pulse generator 22 functions to shape the RF pulses from the RF source 24 into apodized sinc pulses. The RF amplifier 20 and the RF pulse generator 22, and the RF source 24 are each controlled by the computer 200 via an interface circuit 214. Apodized sinc pulses excite the spin states of the nuclei, which store the energy in an excited state, and the excited state decays and releases a pulse of RF energy to be captured in acquisition. Many different pulse sequences can be used, including turbo field echo (TFE), fast field echo (FFE), susceptibility weighted imaging (SWE), short Tau inversion recovery (STIR; also called short $T_1$ inversion recovery—this is a fat suppression technique with an inversion time $TI = T_1 \ln(2)$ where the signal of fat is zero. This equates to approximately 140 ms at 1.5 T), Turbo Spin Echo (TSE), Fast Low Angle Shot (FLASH; a special kind of spin-echo sequence where larger tip angles give $T_1$ weighted images, smaller give more $T_2^*$weighted images), Volumetric Interpolated Brain Examination (VIBE), magnetic pulse rapid gradient echo (MP RAGE), Fluid Attenuation Inverted Recovery (FLAIR), and Parallel Imaging Techniques such as sensitivity encoding (SENSE) and Array coil spatial sensitivity encoding (ASSET) are the most widely used parallel imaging methods (mSENSE from Siemens, ASSET from GE, SENSE from Philips, RAPID from Hitachi and SPEEDER from Toshiba) and involves 4 steps: generate coil sensitivity maps, acquire partial k-space MR data, reconstruct partial field of view images from each coil, and 4) combine partial field of view images by matrix inversion. Additional second and third generation parallel imaging techniques like GRAPPA, Auto-Smash, VD-SMASH which are parallel imaging techniques to speed up MRI pulse sequences using K-space undersampling, and the acquisitions of the additional lines is also a form of calibration, as the coefficients of signals across coils can be determined from the measurements.

The RF detector 26 functions to capture the RF signals, and the simplest form of NMR/MRI/MRSI/MR Signature Detection where the signal is received from the free induction decay of excited spin states, though it is possible to receive many more complex pulse sequences. The RF detector can be a linear analog detector or a quadrature analog detector. Linear analog detectors can capture signals along one vector in the coordinate space (e.g. $M_x$ or $M_y$) and a quadrature analog detector can capture signals along two vectors in the coordinate space (e.g. $M_x$ and $M_y$) simultaneously. The linear analog detector is typically a doubly balanced mixer, and the quadrature analog detector is typically a pair of double balanced mixers, a pair of filters, a pair of amplifiers and a 90-degree phase shifter.

In some embodiments, the RF detector coils can be tuned to receive one or more frequencies, depending on the spectra desired, either a wide-band receiver coil can be used, or a software based or hardware based tuner can be used to automatically tune at least one RF detector coil to receive one or more frequencies from a desired nuclei or molecule.

Figure 3A:
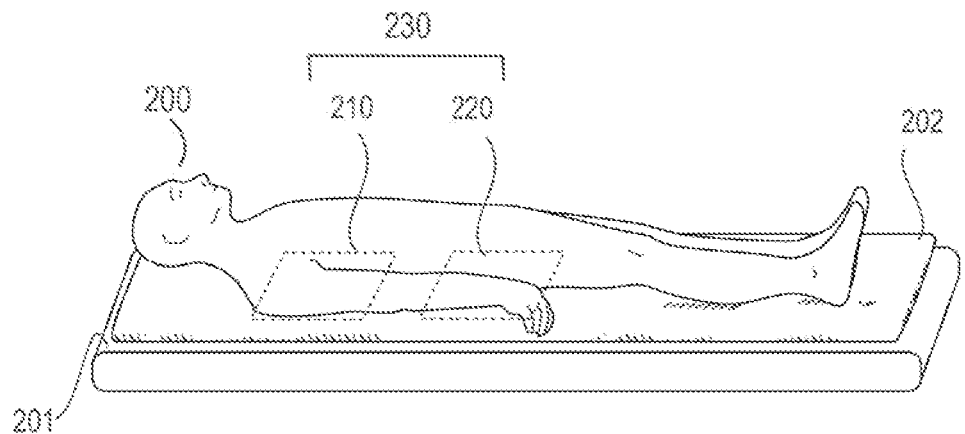
FIG. 3 is a diagram of a subject bed adapted for MR Elastography in accordance with an embodiment of the invention.
Figure 3B:
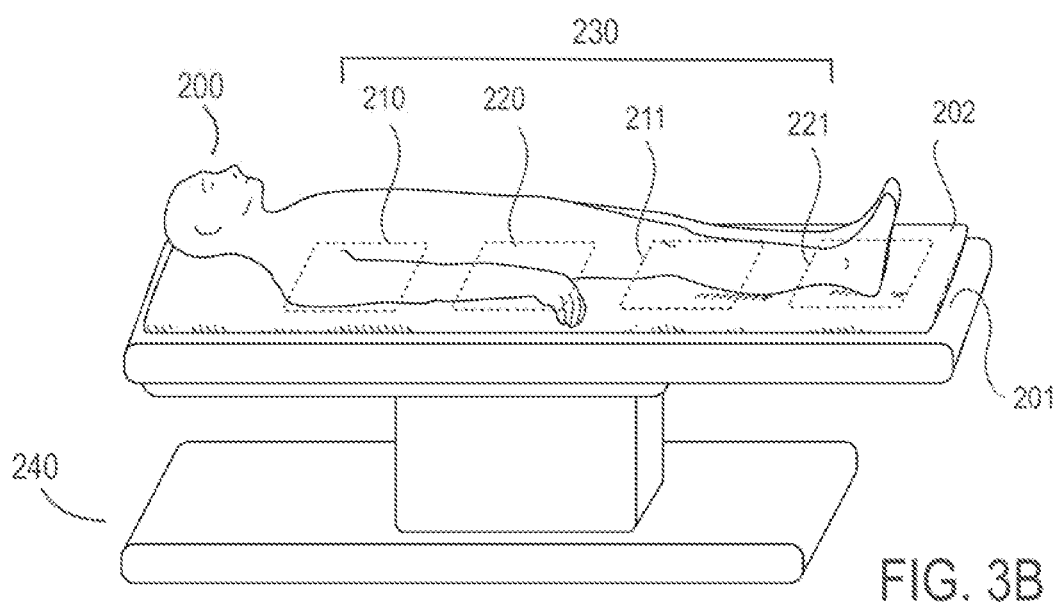
Figure 4A:
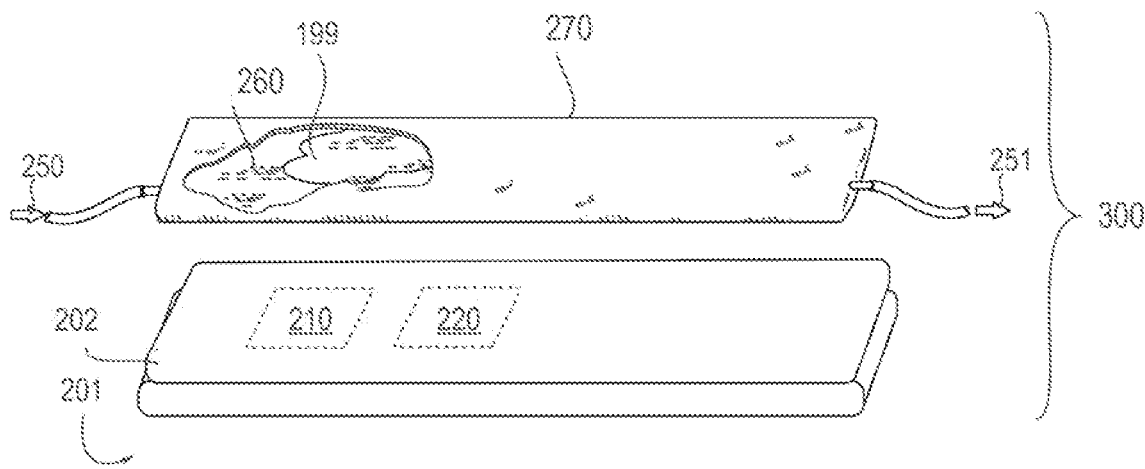
FIG. 4 is a diagram of a sample bed adapted for MR Elastography in accordance with an embodiment of the invention.
Figure 4B:
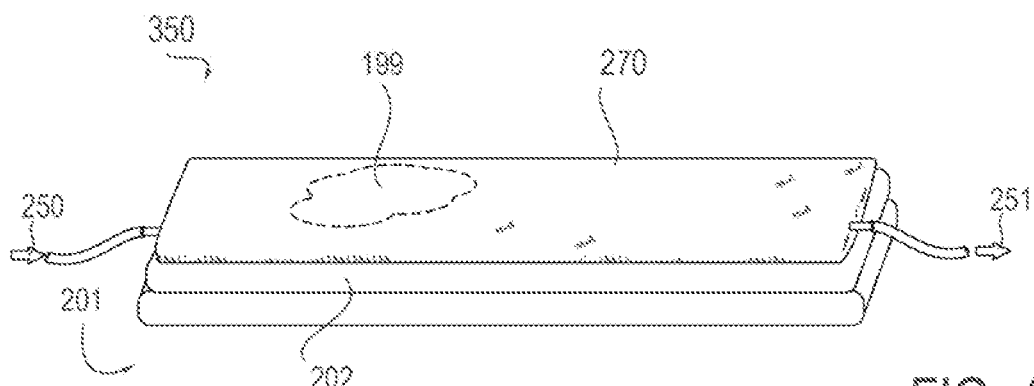

As shown in FIGS. 3-4, the patient table 5 can include embedded RF transmitters and receivers 210, 211, and other components of RF signal transmission and receiver coils embedded in an electromagnetically permeable material 202. In one variation, the patient table 5 can include RF transmitters and receivers 210, 211 embedded in Teflon, Concrete, Wood, Sapphire or another electromagnetically permeably material functioning as a surface of the table. In another variation, the patient table 5 may include, in addition to or instead of an electromagnetically permeable material, a padded material to improve patient comfort, such as an inert semi-rigid polymer like PDMS (poly-dimethyl siloxane). The patient table 5 can be mechanically actuated, moved through the bore of a magnet 2, or moved through a zero field scanner.

In another variation, the surface of the patient table may be constructed from a disposable ultrasound gel pad 202, which can function as a disposable ultrasound standoff (i.e., increases the distance between the transducer face and the area of interest). In another embodiment, as shown in FIGS. 3-4, the RF transmitters and receivers for the RF coils 210, 211, can be embedded next to ultrasound transducers 220, 221 (receivers and transmitters capable of transmitting above the human hearing threshold, typical ultrasound refers to 20 kHz to 1 GHz) in a gel pad material 202 that can function as a transmitter of acoustic energy for ultrasound measurements, and such ultrasound measurements can also be performed during an MR scan, in a process known as MR Elastography. Additional sensors can be embedded in the gel pad 202, including optical sensors, infrared sensors, conductance sensors, and any other suitable sensors.

The gel pad 202 can provide both additional comfort to a patient, thereby improving the patient experience, additional stability to a sample, and can also be disposable. Gel pads can also provide better contact with bony surfaces of the body, open wounds, or other body surfaces that can be challenging for ultrasound probes to reach.

A number of materials will work for the transmission of the ultrasound energy into the target, and it is worth noting that the information captured in the elastogram can be noise tolerant, so the choice of material for the gel pad 202 or patient table need not be made solely based upon electromagnetic permeability or a material's ability to transfer ultrasonic energy, but rather patient comfort, cost, ease of transport, manufacturability, disposability, and sanitary conditions can and should also be considered when choosing this material.

Disposability of the gel pad 202 can improve sanitary conditions, reduce the need for sterilization of surfaces, and reduce the risk of spreading diseases among patients and cross-contamination of samples in diagnostic and therapeutic ultrasound measurements. Gel and gel pads have been demonstrated in the literature to transmit more ultrasound energy than glycerin, mineral oil, or water, and as mentioned in:

Klucinec B. The Effectiveness of the Aquaflex Gel Pad in the Transmission of Acoustic Energy. *Journal of Athletic Training*. 1996; 31(4):313-317.

Gel pads are a particularly practical choice for clinical applications of ultrasound over uneven surfaces.

In some embodiments, the gel pad may comprise . . . .

Further, in another variation, the gel pad may include a substance that conveys imaging phantom attributes to the gel pad. For example, the gel pad may include a substance with a known Proton Density, T1 (i.e., longitudinal relaxation time) and T2 (i.e., transverse relaxation time), so that the gel, at least in part, functions as an imaging phantom.

The gel pad 202 may be manufactured with divots, ribs, or other surface features to interface more tightly with the RF sensors 201, 211 and the ultrasound transducers 220, 221. The gel pad 202 can be molded, laser cut, stamped, or manufactured in any other suitable fashion.

In another variation, as shown in FIG. 3, a portion of a patient's body or a medical sample can be immersed in a vessel of ultrasound gel to provide ample contact to transmit acoustic energy to the tissue sample during an MR scan.

In yet another variation, as shown in FIGS. 3-4, a patient or sample can interface with a gel layer on a gel pad over the embedded ultrasound RF sensors and provide an additional layer of conductance and comfort to a patient.

In one embodiment, in addition to the surface of the patient table having gel, a coil or other sensor interface can be coated with gel or have a gel interface with the patient, for example a clamshell could fold over a patient, a part of a patients body, or a patient or a part of a patient's body could be inserted into the device to have a better conductance for ultrasonic waves from multiple directions, and provide an improved image or data capture quality.

In another embodiment, the composition of the gel can be adjusted to improve or reduce the conductance of ultrasonic waves, and/or improve and or adjust the fit to a patient's body, and the adjustments can be performed by adding or removing water from a gel substance, either before or during a measurement, and alternatively doping a gel with additional chemicals to improve conductance of ultrasonic waves, or to differentiate the ultrasound gel or gel pad 202 from the subject, for example a potassium salt could be added into an ultrasound gel and highlight a concentration of potassium in MR images or MR data capture of an MR Elastography measurement. A further variation, as described elsewhere herein, comprises doping a gel with a substance that has a known proton density.

As shown in FIG. 4, a sample can be positioned and translated through a surface on a surface of gel, using positive or negative pressure in the gel to move the sample across the surface of a table with embedded ultrasound and RF sensors. The gel would flow from fluid source 250 to fluid sink 251 and function as a transport layer to move the sample across the sensor array, and the gel fluid would function as a sheathing between the sample and the sensor array. The samples could be disposed of along with the ultrasound gel, or the samples could be cleaned and repackaged, vacuum-sealed or otherwise processed (FFPE for example). Using the gel as a transport layer across the sensors allows an automation of measurements and a mechanical/physical queuing of sample measurements, which could dramatically increase throughput and productivity for a lab technician or the overall output of a lab facility (whether automated or not). Additionally, multiple samples could be transported in parallel or other packing arrangements to optimally utilize the sensor array to take multiple measurements at once. Similarly, human or animal subjects could also be processed in rapid succession by floating through a sensor array, similar to how patrons of a water park would float through a river ride or a waterslide.

Figure 5A:
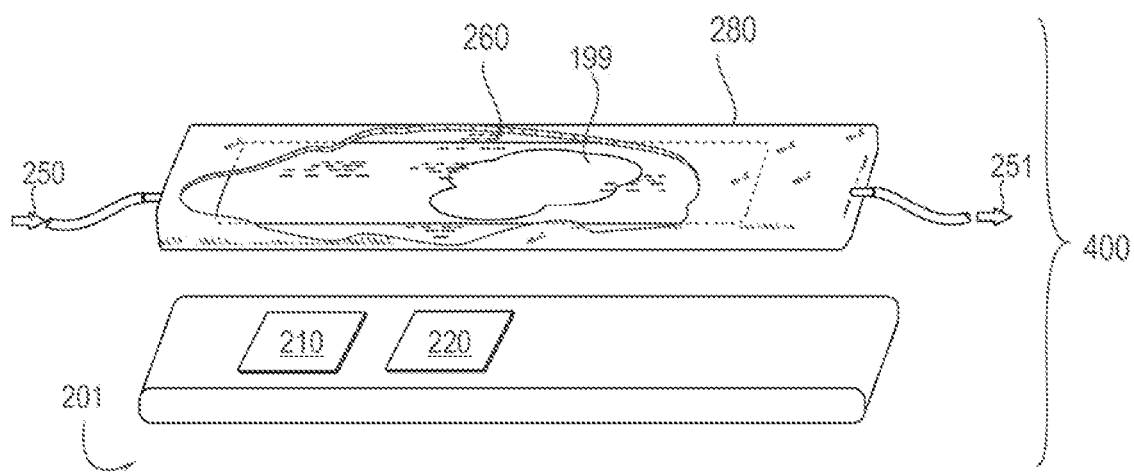
FIG. 5 is a diagram of a flow cell adapted to use ultrasound fluid to sheath samples for MR Elastography in accordance with an embodiment of the invention.
Figure 5B:
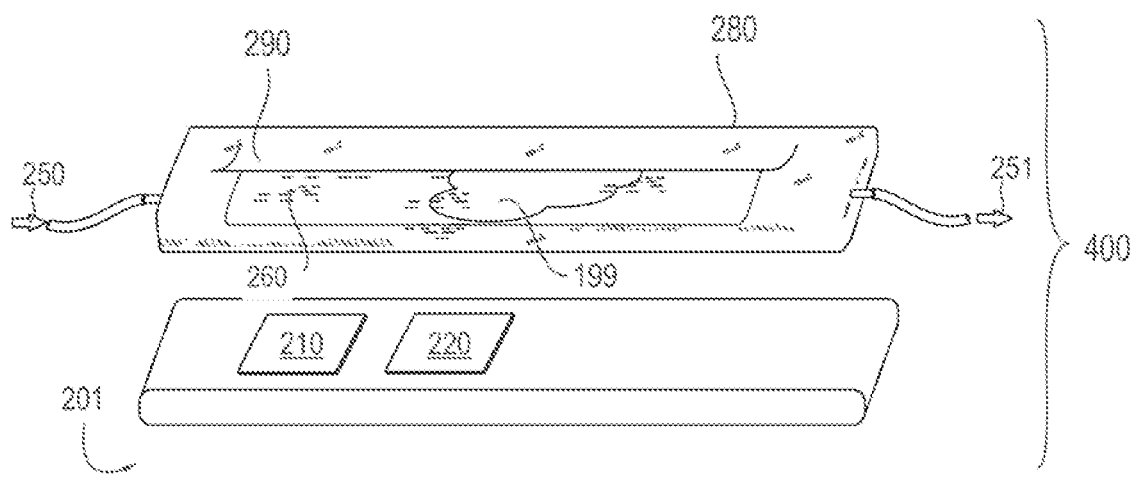
Figure 6A:
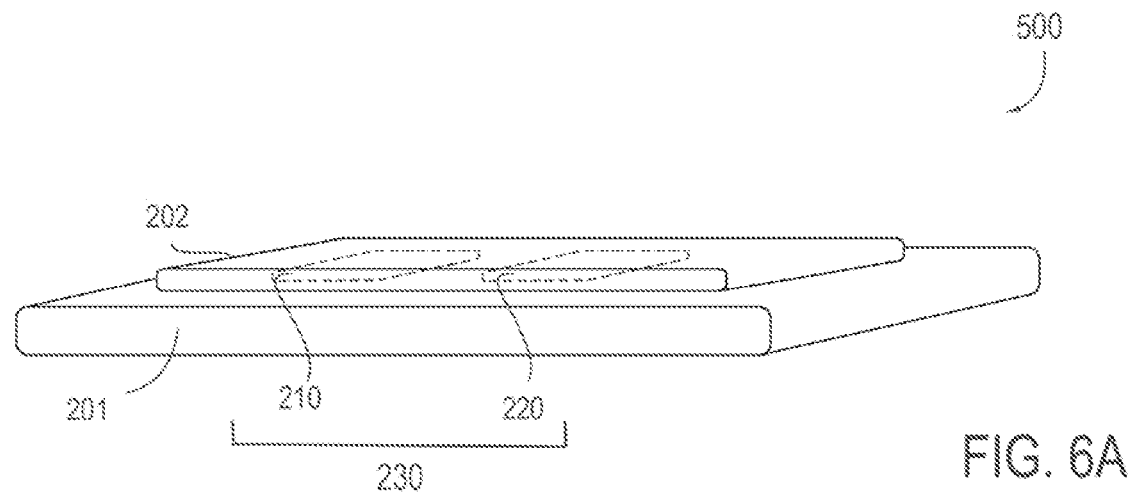
Figure 6B:
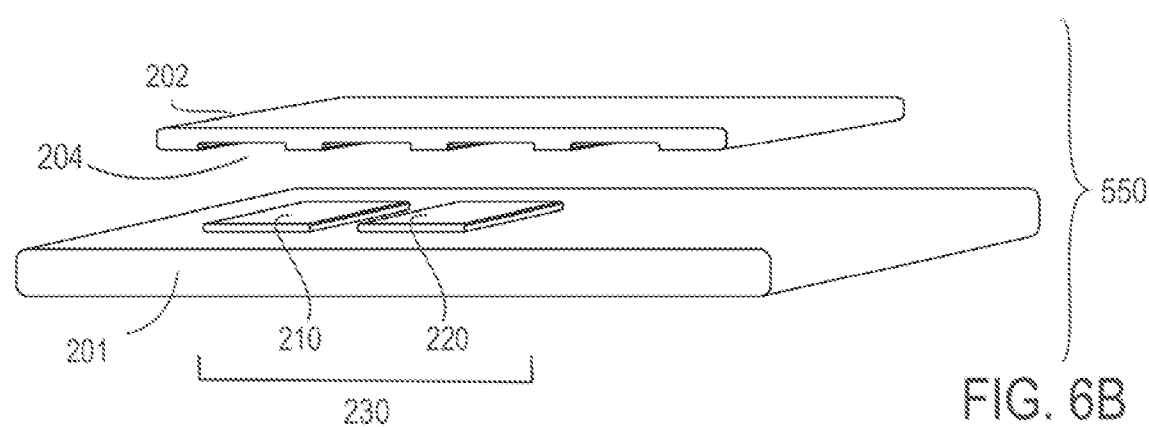
Figure 7:
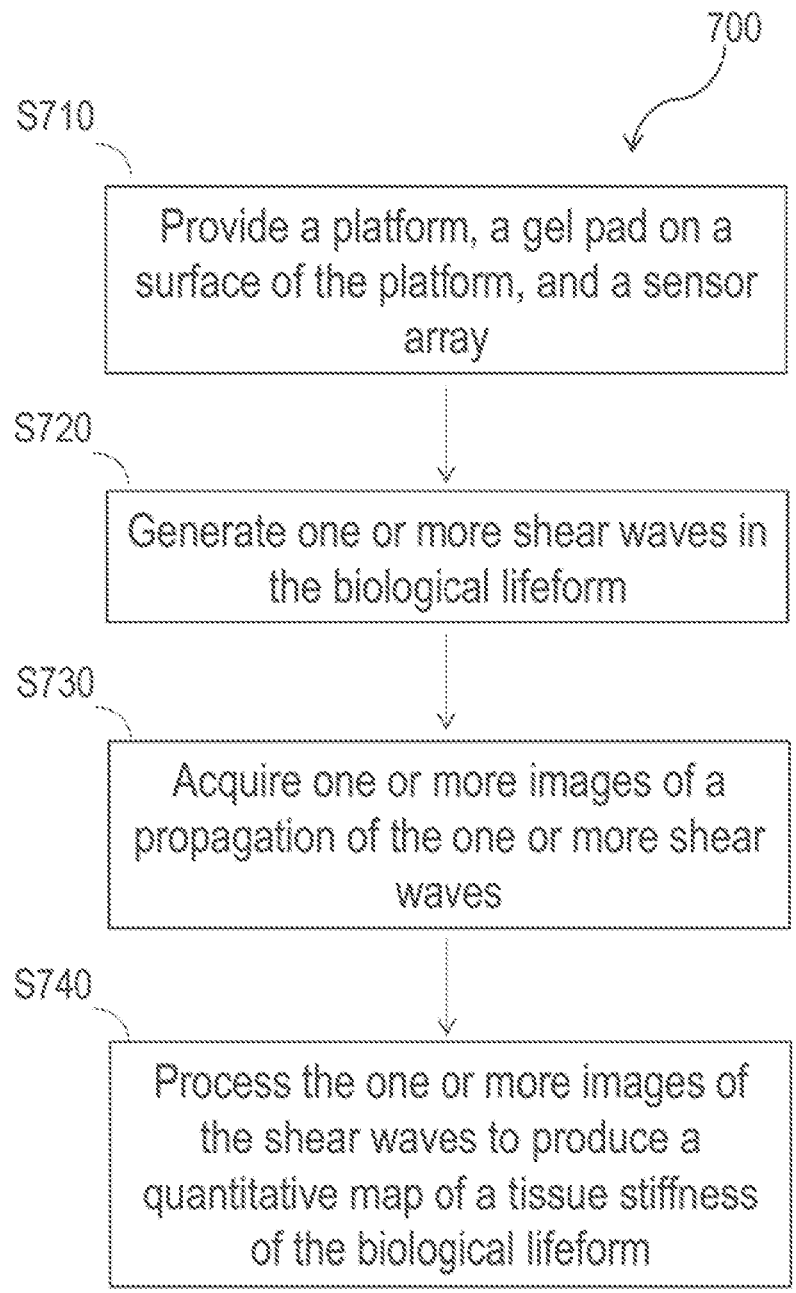

As shown in FIG. 5, a sample can be immersed or sheathed in ultrasound gel, or even water, and translated through a tube using a pump system on each end of a tube to create a positive and/or negative pressure to propel the sheathed sample in ultrasound fluid, enabling a sample to be transported (and also suspended in place) in a vessel, through which ultrasound energy, and RF energy for MR Elastography or other MR and non-MR measurements can be performed on a sample. Such a system could enable many samples to be processed in quick succession and either bottled directly in their sheathing fluid, cleaned of the ultrasound fluid, or disposed of (via incineration or hazardous waste collection), or vacuum sealed for storage, or otherwise processed (FFPE for storage and analysis).

In some embodiments of one or more of the preceding methods, there may be additional or fewer operations. Furthermore, the order of the operations may be changed, and/or two or more operations may be combined into a single operation. In addition, in some of the preceding embodiments there are fewer components, more components, a position of a component is changed and/or two or more components are combined.

In the preceding description, we refer to 'some embodiments.' Note that 'some embodiments' describes a subset of all of the possible embodiments, but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. An apparatus, comprising:
a platform;
a gel pad on a surface of the platform; and
a sensor array comprising:
at least one ultrasound transducer, and
at least one radiofrequency (RF) transmitter and receiver coil, wherein the sensor array is embedded within the gel pad, and the gel pad comprises an aqueous material and is configured to provide mechanical impedance matching between the at least one ultrasound transducer and a biological lifeform;
wherein the aqueous material transmits more ultrasound energy than glycerin, mineral oil or water;
wherein at least the one ultrasound transducer and at least the one RF transmitter are embedded within the gel pad; and
wherein embedded comprises surrounding and having contact with at least three sides of at least the one ultrasound transducer and at least the one RF transmitter; and
wherein, when performing Magnetic Resonance (MR) Elastography measurements on the biological lifeform, the apparatus is configured to:
generate one or more shear waves in the biological lifeform;
acquire one or more images of propagation of the one or more shear waves in the biological lifeform; and
provide information associated with the one or more images that specifies a quantitative map of a tissue stiffness of the biological lifeform.

2. The apparatus of claim 1, wherein the gel pad comprises a surface feature in a location where the gel pad contacts the sensor array.

3. The apparatus of claim 2, wherein the surface feature is one of: a divot, a rib, a groove, a depression, an indentation, or an impression.

4. The apparatus of claim 1, wherein the platform comprises an electromagnetically permeable material.

5. The apparatus of claim 4, wherein the electromagnetically permeable material comprises: Teflon, concrete, wood, sapphire, or poly-dimethyl siloxane.

6. The apparatus of claim 1, wherein the gel pad is configured to function as an imaging phantom.

7. The apparatus of claim 1, wherein a composition of the gel pad comprises a substance with a known proton density.

8. The apparatus of claim 1, wherein a composition of the gel pad comprises a substance with a known longitudinal relaxation time (T1) and a known transverse relaxation time (T2).

9. The apparatus of claim 1, wherein the gel pad comprises a contrast agent.

10. The apparatus of claim 1, wherein the sensor array further comprises one or more of: an optical sensor, an infrared sensor, a conductance sensor, a movement sensor, a fiber optic sensor, a photoplethysmogram sensor, a piezoelectric sensor, or an electrocardiogram sensor.

11. The apparatus of claim 1, wherein the biological lifeform is one of: a tissue sample or a patient.

12. The apparatus of claim 1, wherein the gel pad is configured to increase a distance between the at least one ultrasound transducer and the biological lifeform.

13. A system, comprising:
a Magnetic Resonance (MR) system comprising:
an ultrasonic wave generator;
a computing device, wherein the ultrasonic wave generator is configured to generate one or more shear waves in a biological lifeform;
an interface circuit configured to communicatively couple a sensor array and the ultrasonic wave generator to the computing device;
a platform;
a gel pad on a surface of the platform; and
the sensor array comprising:
at least one ultrasound transducer, and
at least one radiofrequency (RF) transmitter and receiver coil, wherein the sensor array is embedded within the gel pad, and the gel pad comprises an aqueous material and is configured to provide mechanical impedance matching between the at least one ultrasound transducer and the biological lifeform;
wherein the aqueous material transmits more ultrasound energy than glycerin, mineral oil or water;
wherein at least the one ultrasound transducer and at least the one RF transmitter are embedded within the gel pad;
wherein embedded comprises surrounding and having contact with at least three sides of at least the one ultrasound transducer and at least the one RF transmitter; and
wherein, when performing MR Elastography measurements on the biological lifeform, the system is configured to:
generate one or more shear waves in the biological lifeform;
acquire one or more images of propagation of the one or more shear waves in the biological lifeform; and
compute, based at least in part on information associated with the one or more images, a quantitative map of a tissue stiffness of the biological lifeform.

14. The system of claim 13, wherein, when performing the MR Elastography measurements on the biological lifeform, the system is configured to identify an anomaly in the biological lifeform based, at least in part, on the computed quantitative map.

15. The system of claim 13, wherein the system is configured to alter a water content of the gel pad before or during the performing of MR Elastography measurements.

16. The system of claim 13, wherein, when performing the MR Elastography measurements on the biological lifeform, the system is configured to alter: an elasticity, a viscosity of the gel pad or both to alter a surface area of the gel pad in contact with the biological lifeform.

17. The system of claim 13, wherein, when performing the MR Elastography measurements on the biological lifeform, the system is configured to monitor a pulse of the biological lifeform using the sensor array.

18. The system of claim 13, wherein, when performing the MR Elastography measurements on the biological lifeform, the system is configured to measure one or more of: a weight, a volume, or a density of the biological lifeform using the sensor array.

19. The system of claim 13, wherein different regions of the gel pad comprise different concentrations of a doping agent.

20. The system of claim 13, wherein the gel pad comprises a doping agent to differentiate the gel pad from the biological lifeform.

\* \* \* \* \*